United States Patent
Domke et al.

(10) Patent No.: US 9,600,952 B2
(45) Date of Patent: Mar. 21, 2017

(54) METHOD AND APPARATUS FOR EXAMINING A VALUE DOCUMENT

(71) Applicant: GIESECKE & DEVRIENT GMBH, Munich (DE)

(72) Inventors: Jan Domke, Vaterstetten (DE); Ingo Scholz, Bremen (DE)

(73) Assignee: GIESECKE & DEVRIENT GMBH, Munich (DE)

( * ) Notice: Subject to any disclaimer, the term of this patent is extended or adjusted under 35 U.S.C. 154(b) by 219 days.

(21) Appl. No.: 14/365,724

(22) PCT Filed: Dec. 19, 2012

(86) PCT No.: PCT/EP2012/005273
§ 371 (c)(1),
(2) Date: Jun. 16, 2014

(87) PCT Pub. No.: WO2013/091856
PCT Pub. Date: Jun. 27, 2013

(65) Prior Publication Data
US 2014/0352441 A1    Dec. 4, 2014

(30) Foreign Application Priority Data
Dec. 21, 2011  (DE) ......................... 10 2011 121 912

(51) Int. Cl.
*G07D 7/08*  (2006.01)
*G01N 29/44*  (2006.01)

(52) U.S. Cl.
CPC ........... *G07D 7/08* (2013.01); *G01N 29/4454* (2013.01)

(58) Field of Classification Search
CPC  G07D 7/08; G07D 7/06; G07D 7/004; G01N 29/04; G01N 29/07; G01N 29/12; G01N 29/11; G01N 29/4454; G01N 29/46
(Continued)

(56) References Cited

U.S. PATENT DOCUMENTS 6,763,721 B2    7/2004  Wunderer et al.
7,571,796 B2    8/2009  Stenzel et al.
(Continued)

FOREIGN PATENT DOCUMENTS

DE          103 35 147 A1    3/2005
DE    10 2004 036 229 A1    2/2006
(Continued)

OTHER PUBLICATIONS

International Search Report from corresponding International Application No. PCT/EP2012/005273, Mar. 13, 2013.
(Continued)

*Primary Examiner* — Laura Martin
*Assistant Examiner* — Rose M Miller
(74) *Attorney, Agent, or Firm* — Workman Nydegger

(57) ABSTRACT

A method for checking a value document of a specified value-document type has a window which has a foil region. The measurement values for an ultrasound transmission of the value document are established in a spatially resolved manner, and it is checked while employing the measurement values whether for a specified number of locations in a specified checking region the ultrasound transmission according to a specified criterion is greater than a specified minimum ultrasound transmission that is characteristic of a specified portion, lying outside the checking region, of at least one value document of the specified value-document type.

19 Claims, 7 Drawing Sheets

(58) Field of Classification Search
USPC .. 73/597, 298, 599, 600, 645, 646, 648, 659
See application file for complete search history.

(56) References Cited

U.S. PATENT DOCUMENTS

| | | |
|---|---|---|
| 7,607,528 B2 | 10/2009 | Derks et al. |
| 8,510,062 B2 | 8/2013 | Domke et al. |
| 2003/0025512 A1* | 2/2003 | Wunderer ............. G01N 29/11 324/639 |
| 2003/0183012 A1 | 10/2003 | Wunderer et al. |
| 2006/0151282 A1 | 7/2006 | Derks et al. |
| 2007/0187209 A1 | 8/2007 | Stenzel et al. |
| 2009/0074231 A1* | 3/2009 | Rancien ................ D21H 21/40 382/100 |
| 2009/0312957 A1 | 12/2009 | Domke et al. |
| 2010/0060881 A1 | 3/2010 | Kayani |
| 2010/0243729 A1 | 9/2010 | Russell et al. |

FOREIGN PATENT DOCUMENTS

| | | | |
|---|---|---|---|
| DE | 10 2006 033 001 A1 | 1/2008 | |
| WO | 02/10716 A2 | 2/2002 | |
| WO | 2004/055740 A2 | 7/2004 | |
| WO | 2005/013207 A1 | 2/2005 | |
| WO | WO 2008134910 A1 * | 11/2008 | ............... G07D 7/06 |

OTHER PUBLICATIONS

International Preliminary Report on Patentability for International Application No. PCT/EP2012/005273, Jun. 24, 2014.

* cited by examiner

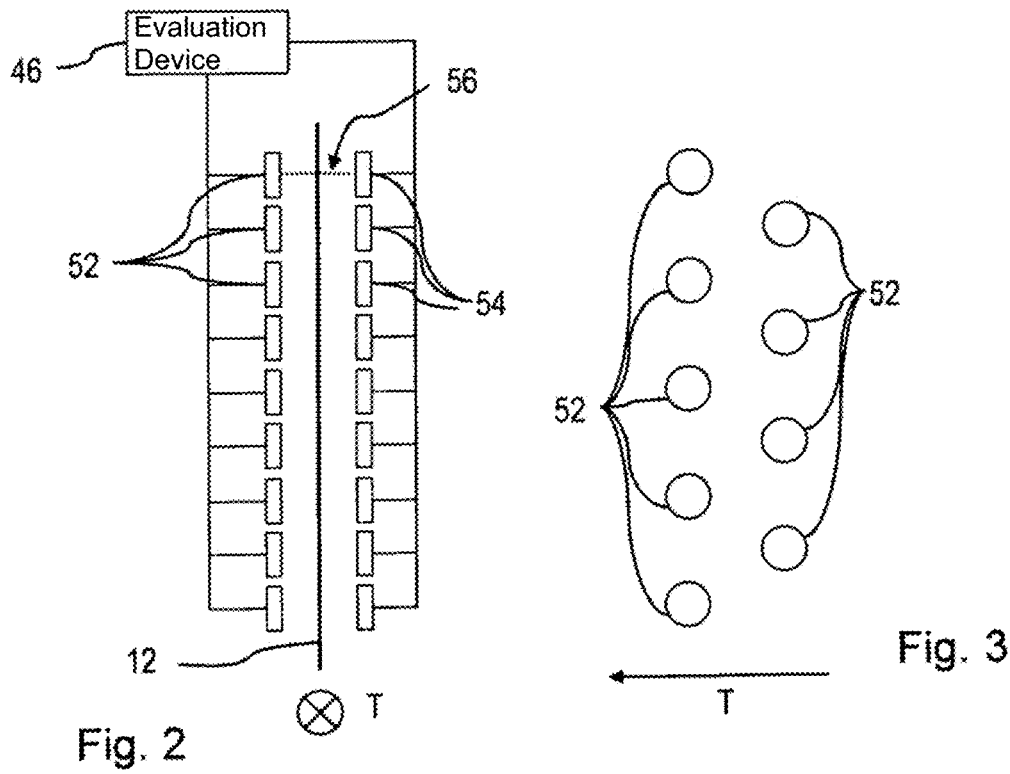
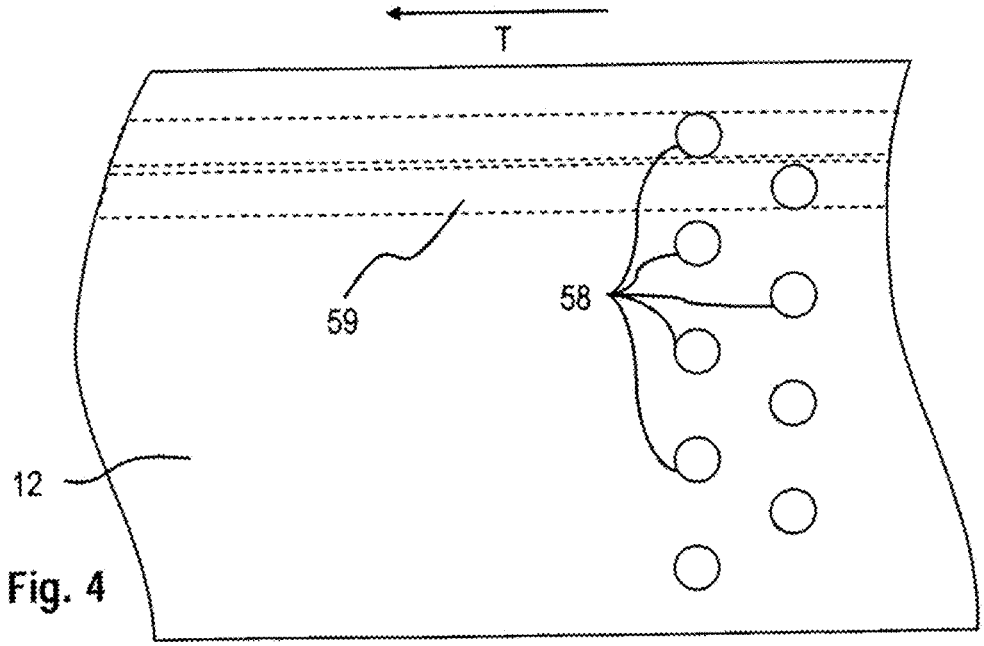

METHOD AND APPARATUS FOR EXAMINING A VALUE DOCUMENT

BACKGROUND

The present invention relates to a method for examining a value document and to a corresponding apparatus for carrying out the method.

Value documents are understood here to be sheet- or card-shaped objects that represent for example a monetary value or an authorization and hence should not be manufacturable arbitrarily by unauthorized persons. Such value documents have features that are not easily manufactured or copied, whose presence is an indication of authenticity, i.e. manufacture by an authorized body Important examples of such value documents are chip cards, coupons, vouchers, checks and in particular bank notes.

Certain value-document types have, as a humanly recognizable security feature, a window which has a special optical property compared to other portions of the value document, for example elevated transparency or translucency.

SUMMARY

The present invention is based on the object of enabling the check of value documents having a window.

This object is achieved by a method according to the claims, and in particular a method for checking a value document of a specified value-document type having a window which has a foil region, wherein measurement values for an ultrasound transmission of the value document are established in a spatially resolved manner, and wherein it is checked while employing the measurement values whether for a specified number of locations in a specified checking region the ultrasound transmission according to a specified criterion is greater than a specified minimum ultrasound transmission that is characteristic of a specified portion, lying outside the checking region, of at least one value document of the specified value-document type.

The object can now in particular consist in carrying out the check for authenticity or the presence of a forgery. In dependence on the result of the check, there can then preferably be formed a signal which represents an indication of the authenticity of the value document and/or which represents an indication of the presence of a forgery of the value document. The signal can be so formed that it represents an indication of the authenticity of the value document only when the specified number of locations having the required ultrasound transmission in the checking region was found, and/or that it represents an indication of the presence of a forgery whenever this number was not found. The signal can in particular also be employed for storing a corresponding authenticity value in a memory of an evaluation device or data processing device employed in the check, said value representing corresponding indications and being employable subsequently.

The object is further achieved by an apparatus for examining a value document of a specified value-document type having a window, said apparatus having an ultrasound transmission sensor for capturing spatially resolved measurement values for the ultrasound transmission in a specified frequency range through the value document, and a control and evaluation device connected to the ultrasound transmission sensor via a signal connection, which is configured for carrying out the method according to the invention. The control and evaluation device is configured in particular for establishing measurement values for an ultrasonic property of the value document in a spatially resolved manner by means of the ultrasound transmission sensor, and checking while employing the measurement values whether for a specified number of locations in a specified checking region the ultrasound transmission according to a specified criterion is greater than a specified minimum ultrasound transmission that is characteristic of a specified portion, lying outside the checking region, of at least one value document of the specified value-document type. Further, it is preferably configured for forming in dependence on the result of the check a signal which represents an indication of the authenticity of the value document and/or which represents an indication of the presence of a forgery of the value document. The signal can be so formed that it represents an indication of the authenticity of the value document only when the specified number of locations having the required ultrasound transmission in the checking region was found, and/or that it represents an indication of the presence of a forgery whenever this number was not found. The signal can in particular also be employed for storing a corresponding authenticity value in a memory of the control and evaluation unit, said value representing corresponding indications and being employable subsequently.

Preferably, the apparatus further comprises a transport device for transporting the value document through the ultrasound transmission sensor, the apparatus being so configured that the transmission values are captured during the transport of the value document through the ultrasound transmission sensor. The control and evaluation device can in particular have a data processing device, which can comprise for example an FPGA and/or a microcontroller and/or a processor and a memory with a data processing program stored therein, which in particular carries out the check, as mentioned hereinabove.

According to the invention, ultrasound is employed for the check. Ultrasound is understood within the framework of the present invention to be sound with a frequency greater than 20 kHz. The ultrasound can be emitted onto the value document continuously or preferably in pulsed fashion. The frequency is understood here, in particular in the case of a pulsed emission, to be the average amplitude value of the emitted ultrasound, i.e. the average over the frequency spectrum, weighted with the frequency-dependent relative amplitude.

For establishing the measurement values for the ultrasound transmission, which will hereinafter also be designated transmission values, the apparatus has the spatially resolving ultrasound transmission sensor which is configured for employment in a specified frequency range. The ultrasound transmission sensor can preferably have mutually opposing ultrasonic transmitters and ultrasonic receivers between which, for capturing the measurement values, the value document is transported through by means of a transport device, the measurement values being captured during the transport through. At a fixed intensity of the ultrasound emitted by the ultrasonic transmitters, the measurement values only need to describe the intensity or amplitude of the ultrasound received by the respective ultrasonic transducers. It is also possible, however, that the measurement values have a ratio of received intensity of the transmitted ultrasound and intensity of the transmitted ultrasound.

Preferably, the ultrasound possesses a frequency in the range of 50 kHz to 800 kHz, particularly preferably between 150 kHz and 600 kHz. The ultrasonic sensor is then preferably configured for emitting ultrasound with a frequency between 50 kHz to 800 kHz, particularly preferably between 150 kHz and 600 kHz.

According to the invention, it is checked while employing the measurement values whether for a specified number of locations in a specified checking region the ultrasound transmission according to a specified criterion is greater than the minimum ultrasound transmission.

The checking region can be specified here in dependence on the value-document type and preferably the position of the value document upon capture of the ultrasound transmission. The position of the value document is understood here to be which side of the value document points in a specified direction, for example orthogonally to a plane of the value document, upon capture of the ultrasound transmission, e.g. upward, and which of the edges of the value document is leading in the transport direction. The checking region is so chosen that, with consideration of typical manufacturing-based fluctuations in the position of the window on or in the value document, the window can be captured with a high degree of certainty, i.e. the window lies in the checking region. The checking region is hence preferably larger than the window.

The checking region can be fixed while employing specified authentic reference value documents of the specified value-document type, and be specified for each of the positions.

The method can then comprise the step that a position of the value document is established upon capture of the ultrasound transmission, and the checking region is specified in dependence on the established position.

The apparatus can for this purpose comprise a device for establishing the position of the value document upon capture of the ultrasound transmission, and the control and evaluation device be so configured that the checking region is specified in dependence on the established position. The position can be established for example by means of an optical sensor, for example a remission sensor, which then constitutes the stated device. Alternatively, it is possible to specify a checking region for each position and to carry out the check for each of the checking regions.

It is also possible, however, that a digital image of the value document is captured by means of an optical sensor, and the checking region is specified while employing the image. For this purpose, the window can preferably be searched for and its position and size established in the digital image, which within the framework of the present invention through pixel data for pixels of the image that are captured by means of the optical sensor. These data can then be employed for establishing the checking region, which can for example be larger in every direction by a specified value than the optically recognized window. The apparatus can for this purpose comprise an optical sensor for capturing an optical image, preferably a transmission image, of the value document and forming a digital image, and the control and evaluation device can preferably be configured for specifying the checking region while employing the image. This embodiment is particularly suited for windows that are well recognizable in images of an optical sensor, for example see-through windows. Optical radiation is understood here to be radiation in the ultraviolet, visible or infrared wavelength region. The sensor operating with optical radiation only needs to operate in at least one specified wavelength region for optical radiation. This development has the advantage that the position of the value document does not need to be known The minimum ultrasound transmission or a corresponding value is so chosen here that it is characteristic of a specified portion of a value document of the specified type that lies outside the checking region. For example, this may be a portion in which no security features changing the ultrasound transmission, such as for example watermarks, are present. As the minimum ultrasound transmission there can be employed for example an average over the location-dependent ultrasound transmission in the portion.

The specified number is preferably chosen in dependence on the extension of the window or the value-document type and the spatial resolution of the ultrasonic sensor or the ultrasound transmission measurement. Preferably, the number is greater than 10.

The measured ultrasound transmission is fixed here by the measurement values in a specified manner or is represented by the same. Accordingly, there is a threshold value corresponding to the minimum ultrasound transmission.

The criterion employed for the check is chosen basically arbitrarily, but suitably.

Thus, the criterion can consist in whether the respective measurement value is greater than the minimum ultrasound transmission value. However, it is also possible to employ, instead of the measurement value, a function value of a function of the measurement value for the measurement value, said function being monotonic, preferably strictly monotonic, in the relevant values range. Then the criterion involves a comparison with a function threshold value which corresponds to the value of the function for the threshold value. The function does not need to be monotonically increasing, it can also be monotonically decreasing. In the latter case, it is then checked whether the function value for the respective measurement value is smaller than the function threshold value.

Further, the check of the criterion for a respective location can comprise a formation of an average of the ultrasound transmission for the location and of the ultrasound transmissions over at least two, preferably at least four, locations directly neighboring to the respective location. In particular, the criterion can comprise that the ultrasound transmission for a location is greater than the minimum ultrasound transmission when an average of the ultrasound transmission over the respective location and at least two directly neighboring locations, preferably at least four directly neighboring locations, is greater than the minimum ultrasound transmission.

Further, the criterion can preferably involve the ultrasound transmission being greater than the minimum ultrasound transmission by a specified value. This value can be chosen in principle arbitrarily, but suitably. Preferably, it is chosen in dependence on the value-document type and in particular the kind of window and the ultrasound transmission properties of value documents of the specified type in the specified portion. Further, it can preferably be so chosen that random fluctuations or noise when measuring the ultrasound transmission have only a weak influence, or particularly preferably no influence, on the result of the check.

The method and in particular the check can be carried out by means of the control and evaluation device, which can for this purpose comprise an electronic circuit or preferably a data processing device, which can have for example an FPGA and/or a microcontroller and/or a processor. In the case that a data processing device is employed, the latter can comprise a processor or microcontroller and a memory which stores instructions for a computer program upon whose execution by the processor or microcontroller the method is carried out while employing the sensor.

As mentioned hereinabove, the minimum ultrasound transmission can be established for a portion of at least one value document. According to a preferred embodiment, the specified minimum ultrasound transmission can be established by examinations of reference value documents of the specified value-document type. This allows a fast and simple evaluation upon a check.

Alternatively, it can also be preferred that before the check the specified minimum ultrasound transmission is established while employing measurement values captured for the value document. In particular, there can be employed measurement values for locations in the specified portion of the value document. This embodiment offers the advantage that manufacturing- or use-based fluctuations in the ultrasound transmission properties of the value documents have a less strong influence on the check.

In both cases the control and evaluation device is then configured accordingly.

A particularly reliable check results when the check involves establishing whether the respective ultrasound transmission lies within a specified interval whose lower limit is greater than the specified minimum ultrasound transmission. Preferably, the lower limit is so chosen that the one ultrasound transmission that is greater than the lower limit is greater than the minimum ultrasound transmission according to the specified criterion. By how much the lower limit is greater than the minimum ultrasound transmission can hence preferably be chosen in dependence on the criterion. The upper limit is preferably so chosen that measurement values that occur upon the measurement and would be established upon transmission through a hole in the value document or in the absence of a value document definitely lie outside the interval. Particularly preferably, the upper limit is chosen in dependence on the ultrasound transmission properties of the window, for example for at least one specified reference value document of the specified type. In particular, the upper limit can be given by the maximum transmission stated in the preceding paragraph. Then it is unnecessary to carry out a separate check for whether the ultrasound transmission exceeds the maximum transmission.

The window of the value document can itself have defects, for example tears or holes. Hence, there is also the object to be achieved of checking a window of a value document for its state, preferably possible defects. Preferably, in the method, it is hence checked whether for locations in the checking region the ultrasound transmission is greater than a specified maximum transmission which is preferably greater than an ultrasound transmission that is characteristic of locations in a window of an undamaged value document of the specified value-document type. If the check yields that the ultrasound transmission for at least one of the locations exceeds the maximum transmission, there can particularly preferably be formed and emitted an indication signal which displays that the window is damaged. For this purpose, the control and evaluation device of the apparatus can be configured accordingly. The maximum transmission is preferably specified in dependence on the value-document type. Further, it is preferably so chosen that it is greater by a specified factor, which is preferably greater than 1.1, than the maximal ultrasound transmission of those regions of a new value document of the specified value-document type that have no holes. In this manner it is possible to recognize defects on the window, for example tears or holes.

In principle, it is sufficient, in the method, that the check only involves checking the presence of the specified number of locations for which the ultrasound transmission according to the criterion is greater than the minimum ultrasound transmission. It is also possible, however, that, in the method, the check also involves taking into consideration the distribution of those locations in the specified checking region for which the ultrasound transmission is greater than the minimum ultrasound transmission. In the apparatus, the control and evaluation device is for this purpose preferably so configured that the check also involves taking into consideration the distribution of those locations in the specified checking region for which the ultrasound transmission is greater than the minimum ultrasound transmission. Preferably, it is checked for this purpose whether the distribution of those locations in the specified checking region for which the ultrasound transmission is greater than the minimum ultrasound transmission satisfies a specified distribution criterion. The check can then be classified as successful only when the distribution satisfies a specified distribution criterion. Preferably, the signal is then so formed that it represents an indication of the authenticity of the value document only when the distribution satisfies the specified distribution criterion, or that it represents an indication of the presence of a forgery whenever the distribution does not satisfy the specified distribution criterion. The specified number must then be additionally reached. The distribution can in particular be determined by the form of the window or a pattern in the window.

Further, in the method, the further criterion can additionally be checked of whether the locations corresponding to the specified number of ultrasound transmissions form a contiguous structure. Preferably, the signal is then so formed that it represents an indication of the authenticity of the value document only when the further criterion is satisfied, or that it represents an indication of the presence of a forgery whenever the further criterion is not satisfied. In the apparatus, the control and evaluation device can then be configured accordingly.

Alternatively, in the method, the further criterion can additionally be checked of whether the locations for which the ultrasound transmission is greater than the minimum ultrasound transmission and/or for which the ultrasound transmission lies within the specified interval form a contiguous structure. Preferably, the signal is then so formed that it represents an indication of the authenticity of the value document only when the further criterion is satisfied, or that it represents an indication of the presence of a forgery whenever the further criterion is not satisfied. In the apparatus, the control and evaluation device can then be configured accordingly.

If, in the method, it is also checked whether locations are present for which ultrasound transmission lies above the maximum transmission, it can preferably also be checked additionally whether a plurality of locations for which the ultrasound transmission is greater than the maximum transmission form a contiguous structure. Preferably, the signal is then so formed that it represents an indication of an undamaged state of the window of the value document only when the further criterion is satisfied, or that it represents an indication of a damaged state of the window of the value document whenever the further criterion is not satisfied. In the apparatus, the control and evaluation device can then be configured accordingly.

A window is understood within the framework of the present invention to be a feature of a value document that comprises a hole in a substrate of the value document and at least one foil covering the hole, or that is given by a region of a value document having a polymer substrate, said region having no opacifying layer. The substrate is understood here to be in particular that layer of the value document that is preferably thickest and acts as a carrier.

In the first case, in the method, the window can be in particular a window that comprises a hole in a paper substrate or hybrid substrate of the value document and at least one foil covering the hole, or is formed by the hole and the foil.

In the second case, in the method, the window can be given by a region of a value document having a polymer substrate, said region carrying no opacifying layer. An opacifying layer is understood to be, besides a layer applied with a coating method, preferably a printing method, also a layer made of bank-note paper.

The window preferably has a surface area that is greater than 4 mm$^2$, particularly preferably greater than 16 mm$^2$. This allows a reliable recognition, on the one hand, and an interesting design of the value document, on the other hand.

The covering foil or the region without an opacifying layer can be transparent, but also have optically active structures, for example embossings or holograms.

The subject matter of the invention is also an apparatus for processing value documents having a feeding device for feeding singled value documents, an output device for receiving processed value documents, a transport device for transporting singled value documents, fed by the feeding device, along a transport path from the feeding device to the output device, and an examination apparatus according to the invention, wherein the transport path extends through the ultrasound transmission sensor, with the processing apparatus being configured for processing, preferably sorting, the value documents in dependence on signals of the examination apparatus.

BRIEF DESCRIPTION OF THE DRAWINGS

The invention will hereinafter be explained further by way of example with reference to the drawings. There are shown:

FIG. 2 a schematic representation of an ultrasonic sensor of the bank-note processing apparatus in FIG. 5 with a control and evaluation device in a view along a transport direction of value documents, FIG. 3 a schematic representation of ultrasonic transmitters of the ultrasonic sensor in FIG. 3 in a plane parallel to the plane of a value document to be examined, FIG. 4 a schematic partial representation of a value document with spots or sensing regions acoustically irradiated by the ultrasonic transmitters of the ultrasonic sensor in FIG. 3, FIG. 5 a schematic representation of a value document with locations or sensing regions for which transmission values have been established by means of the ultrasonic sensor in FIG. 3, FIG. 6 a schematic representation of a value document in the form of a bank note having a bank-note paper substrate and a window, FIG. 7 a cross section through the value document of FIG. 1 along the line I-I, FIG. 8 a schematic representation of a value document in the form of a bank note having a polymer substrate and a window, FIG. 9 a cross section through the value document of FIG. 1 along the line I-I, FIG. 10 a simplified flowchart of a method for examining a value document by means of the ultrasonic sensor and the control and evaluation device in FIG. 6 according to a preferred embodiment of the invention, FIG. 11 a schematic representation of the course of the ultrasound transmission for a track along a value document having a window which is partly covered by the track, FIG. 12 a simplified flowchart of a method for examining a value document by means of the ultrasonic sensor and the control and evaluation device in FIG. 6 according to a further preferred embodiment, FIG. 13 a simplified flowchart of a method for examining a value document by means of the ultrasonic sensor and the control and evaluation device in FIG. 6 according to yet another preferred embodiment of the invention, FIG. 14 a schematic representation for illustrating the production of a checking region from a window in a digital image of a value document, FIG. 15 a simplified flowchart of a method for examining a value document by means of the ultrasonic sensor and the control and evaluation device in FIG. 6 according to yet another preferred embodiment, and FIG. 16 a schematic representation of the course of the ultrasound transmission for a track along a value document having a window which is partly covered by the track and has a tear crossing the track.

DETAILED DESCRIPTION OF VARIOUS EMBODIMENTS

Figure 1:
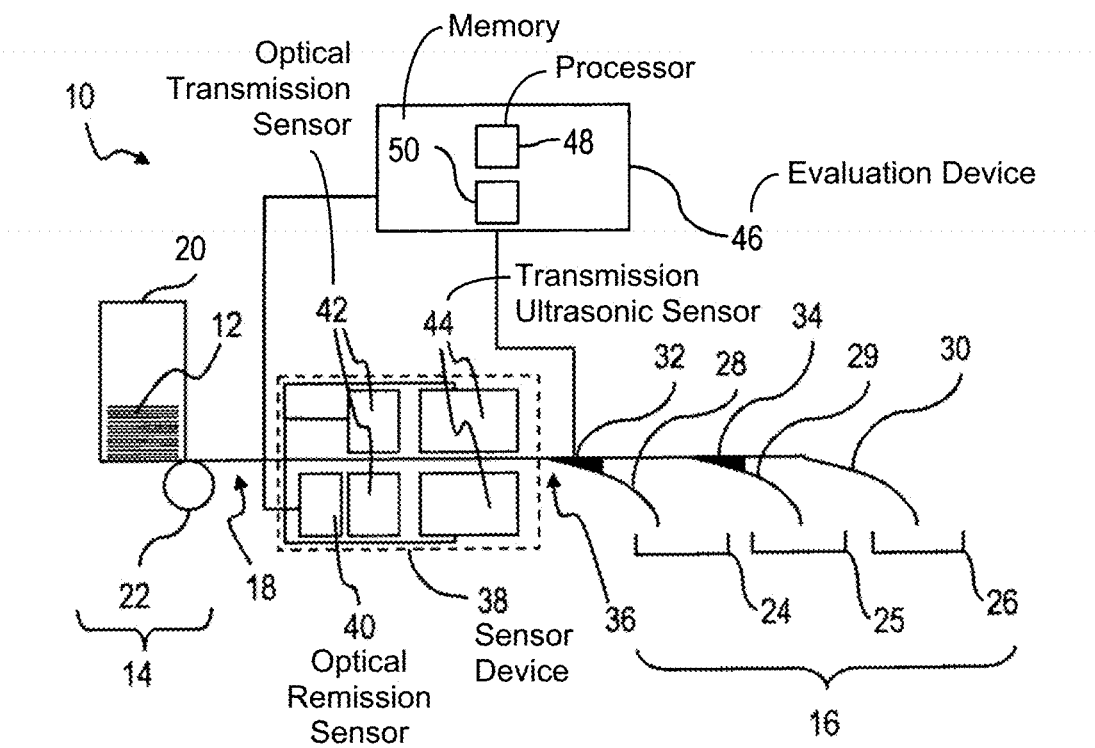
FIG. 1 a schematic representation of a bank-note processing apparatus.

A value-document processing apparatus 10 in FIG. 1, in the example an apparatus for processing value documents 12 in the form of bank notes, is configured for sorting value documents in dependence on the recognition of the authenticity of processed value documents.

It has a feeding device 14 for feeding value documents, an output device 16 for receiving processed, i.e. sorted, value documents, and a transport device 18 for transporting singled value documents from the feeding device 14 to the output device 16.

The feeding device 14 comprises, in the example, an input pocket 20 for a value-document stack, and a singler 22 for singling value documents out of the value-document stack in the input pocket 20.

The output device 16 comprises, in the example, three output portions 24, 25 and 26 into which processed value documents can be sorted according to the result of the processing. In the example, each of the portions comprises a stack pocket and a stacking wheel (not shown) by means of which fed value documents can be deposited in the stack pocket.

The transport device 18 has at least two, in the example three, branches 28, 29 and 30 at whose ends one of the output portions 24, 25, 26 is respectively disposed, and, at the branching points, gates 32 and 34 controllable by actuating signals for feeding value documents to the branches 28 to 30 and thus to the output portions 24 to 26 in dependence on actuating signals.

On a transport path 36, defined by the transport device 18, between the feeding device 14, in the example more precisely the singler 22, and the first gate 32 after the singler 22 in the transport direction there is disposed a sensor device 38 which measures physical properties of the value documents when value documents are being transported past, and forms sensor signals representing the measurement results. In this example, the sensor device 38 has three sensors, namely an optical remission sensor 40 which captures a remission color image of the value document, an optical transmission sensor 42 which captures a transmission image of the value document, and a transmission ultrasonic sensor 44 which captures or measures ultrasound transmission properties of the value document in a spatially resolved manner.

A control and evaluation device 46 is connected via signal connections to the sensor device 38 and the transport device 18, in particular the gates 32 and 34. In connection with the sensor device 38, it classifies a value document in one of specified authenticity classes in dependence on the sensor signals of the sensor device 38 and, by emitting actuating signals, so actuates the transport device 18, here more precisely the gates 32, 34, that the value document is output, in accordance with its class established upon the classification, to an output portion of the output device 16 that is associated with the class. The association with one of the specified authenticity classes, or the classification, is effected here in dependence on at least one specified authenticity criterion. As authenticity classes there are provided classes for value documents recognized as authentic, value documents recognized as forgeries, and value documents for which a suspicion of forgery was established.

The control and evaluation device 46 has for this purpose in particular, besides corresponding interfaces for the sensor device 38 or its sensors, a processor 48 and a memory 50 which is connected to the processor 48 and stores at least one computer program with program code upon whose execution the processor 48 controls the apparatus or evaluates the sensor signals, in particular for establishing an authenticity class of a processed value document, and actuates the transport device 18 in accordance with the evaluation.

More precisely, while the value document is being transported past, the sensors capture, in accordance with their function, sensing-region properties of sensing regions on the bank note that are determined by the relative position of the sensors to the bank note, whereby the corresponding sensor signals are formed. Each of the sensors can have a different spatial resolution, i.e. the size and distribution of the captured sensing regions on the bank note can vary in dependence on the respective sensor and the transport speed employed. Each of the sensing regions has associated therewith a location that represents the position of the sensing regions for the respective sensor relative to each other and/or relative to the bank note.

The control and evaluation device 46 then establishes from the analog or digital sensor signals of the sensors of the sensor device 38 upon a sensor-signal evaluation at least one sensing-region property and/or at least one value-document property that is relevant for testing the bank notes with respect to their authenticity. Preferably, a plurality of these properties are established. In this example, there are established a transmission image and a remission image as optical sensing properties, and the ultrasound transmission of the sensing regions as an acoustic property.

In dependence on the sensing-region properties, the control and evaluation device 46 establishes for the different sensors respective authenticity signals that represent whether or not the established sensing-region or value-document properties represent an indication of the authenticity of the value document. In consequence of these signals, corresponding data can be stored in the control and evaluation device 46, for example the memory 50, for later employment. In dependence on the authenticity signals, the control and evaluation device 46 then establishes an overall result for the authenticity check according to a specified overall criterion, and forms the control signal for the transport device 18 in dependence on the result.

For processing value documents 12, value documents 12 inserted into the input pocket 20 as a stack or singly are singled by the singler 22 and fed in singled form to the transport device 18, which transports the singled value documents 12 past the sensor device 38. The latter captures the properties of the value documents 12, whereby sensor signals are formed which represent the properties of the respective value document. The control and evaluation device 46 captures the sensor signals, establishes in dependence thereon an authenticity class of the respective value document, and so actuates the gates in dependence on the result that the value documents are transported in accordance with the established authenticity class into an output portion associated with the respective authenticity class.

For establishing an authenticity class on the basis of ultrasonic properties there is used the transmission ultrasonic sensor 44, which, in the example, is constructed as follows (cf. FIGS. 2 and 3).

The sensor 44 has a plurality of ultrasonic transducers 52 disposed both transversely to a transport direction T of the value documents 12 and longitudinally thereto substantially in a plane parallel to a direction along the transport path 36 of the transported value document 12, and actuated by the control and evaluation device 46, for emitting ultrasonic pulses onto the bank note. These ultrasonic transducers 52 thus serve at least as ultrasonic transmitters.

Opposite the ultrasonic transducers or transmitters 52 relative to the transport path 36 are the same number of ultrasonic transducers 54 serving as ultrasonic receivers, which are connected to the control and evaluation device 46 via interfaces not shown in the figures and schematically shown signal connections, so disposed that they can receive ultrasonic waves that emanate from a value document 12 transported along the transport path 36 and are caused by acoustic irradiation with ultrasonic pulses of the ultrasonic transmitters 52.

Each of the ultrasonic transmitters 52 has associated therewith one of the ultrasonic receivers 54 such that there results therebetween an ultrasonic path 56 extending at least approximately orthogonally to a value document 12 transported along the transport path 36, along which ultrasonic path an ultrasonic pulse emitted by the respective ultrasonic transmitter 52 runs to the ultrasonic receiver 54 associated therewith. With each pair of ultrasonic transmitters and ultrasonic receivers associated therewith or with each ultrasonic path 56 in connection with the control and evaluation device 46, it is thus possible to establish a value for the ultrasound transmission of the value document 12 at the location acoustically irradiated with the ultrasound.

The ultrasonic transducers 52, 54 are so configured that they are well suited for emitting or receiving ultrasonic pulses with a duration in the range of about 30 μs, in the example, and an ultrasonic frequency, i.e. a frequency maximum of the spectrum of the ultrasonic pulse, of about 400 kHz, in the example. Further, they are so dimensioned that a respective spot 58, i.e. sensing region, acoustically irradiated upon acoustic irradiation with the ultrasonic pulses on a value document 12 transported along the transport path 36 has a diameter of about 2 mm. Each of the sensing regions has associated therewith, as the location, the center of the sensing region.

The ultrasonic transmitters 52 and ultrasonic receivers 54 are so disposed in a plane parallel to the value document 12 in the transport path 36 that values for the ultrasound transmission are capturable for strip-shaped capture regions 59 extending parallel to the transport direction T, as represented in FIG. 4 for an instantaneous view during capture.

Figure 5:
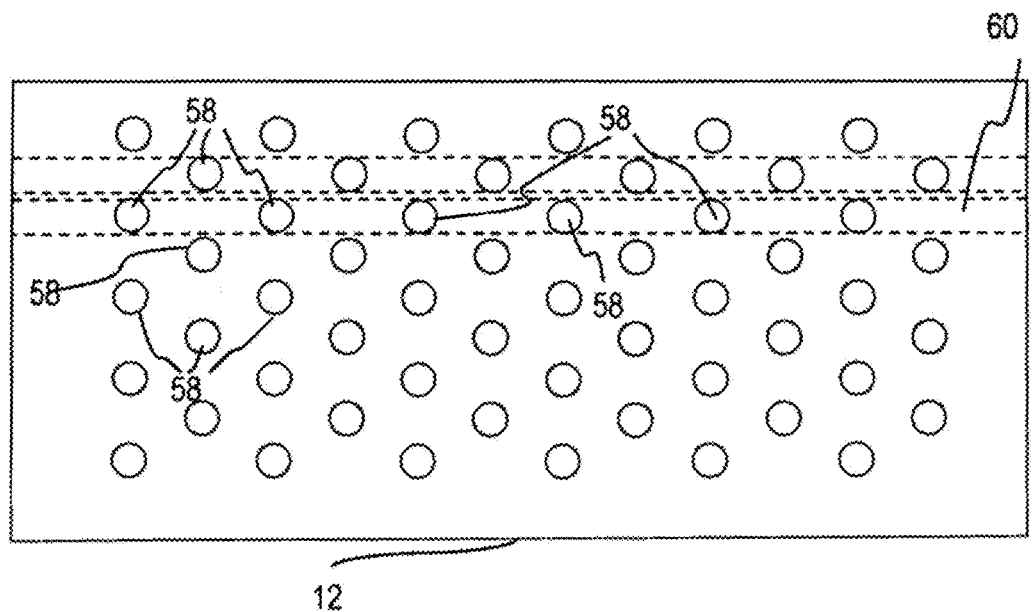

Altogether, there can thus result a distribution, represented for a value document 12 schematically in FIG. 4 and in particular FIG. 5, of sensing regions 58 or locations for which measurement values for the ultrasound transmission, also designated transmission values hereinafter, are capturable when the value document 12 is transported through the ultrasonic paths 56 at a constant, suitably specified speed and transmission values are captured at specified time intervals during said transport. In this exemplary embodiment, the actuation is effected independently of the entry of a value document 12 into the capture region of the transmission ultrasonic sensor 44. To suppress an unwanted reception of ultrasonic pulse echoes, the respective ultrasonic receiver for an ultrasonic path can be switched on at a delay of somewhat less than the pulse transit time for the ultrasonic path, relative to the time when the ultrasonic pulse is emitted by the ultrasonic transmitter for the ultrasonic path, and be switched off again before twice the pulse transit time since emission.

There thus results a regular arrangement of the sensing regions 58 or locations on the value document 12, in the example a substantially hexagonal arrangement. The arrangement of the ultrasonic transmitters 52 and ultrasonic receivers 54 is so chosen that the distance between consecutive locations in at least one of the strips or capture regions 59 is smaller than 1 cm, preferably smaller than 5 mm. In the example, the distance of nearest neighboring locations amounts to about 3 mm, preferably 2 mm.

The sensor 44 has in the exemplary embodiment in particular twenty-four ultrasonic transmitter/receiver pairs or ultrasonic paths 56, which are so disposed that the capture regions 59 or the tracks have a distance between 3 and 4 mm.

For capturing the transmission values, i.e. the transmission, the control and evaluation device 46 captures at constant time intervals the sensor signals of the ultrasonic receivers 54 which represent the intensity or power of individual receiving ultrasonic pulses as a function of time and thus, due to the constant transport speed, also of location. Using these signals, the control and evaluation device 46 also establishes the entry of a value document into the capture region of the sensor 44. The transmission values are given here simply by the received ultrasonic pulse energies, assuming a basically constant transmit power of the ultrasonic transmitters 52. In other exemplary embodiments, however, it is also possible to divide the received ultrasonic pulse energies by a specified or measured ultrasonic pulse energy of transmitted pulses and thus obtain normalized transmission values.

The established transmission values are stored in association with the locations for which they were captured. This can be effected for example in such a way that the transmission values are stored in the memory 50 in the time sequence of their capture separately for each of the capture regions 59. The capture region 59 then corresponds to a coordinate in a direction transverse to the transport direction, and the position in the row along the capture region 59 to a coordinate in transport direction T. An index stating the position in the row, together with the rule for translating locations into the row, then represents the location information.

The frequency at which the ultrasonic pulses are successively emitted and the transport speed of the bank note are so chosen that at least five transmission values are captured in each capture region 59 along the transport direction of the bank note. In the example, transmission values are captured at an interval of 3 mm, preferably 2 mm, along the transport direction, or fifty or more transmission values.

Figure 10:
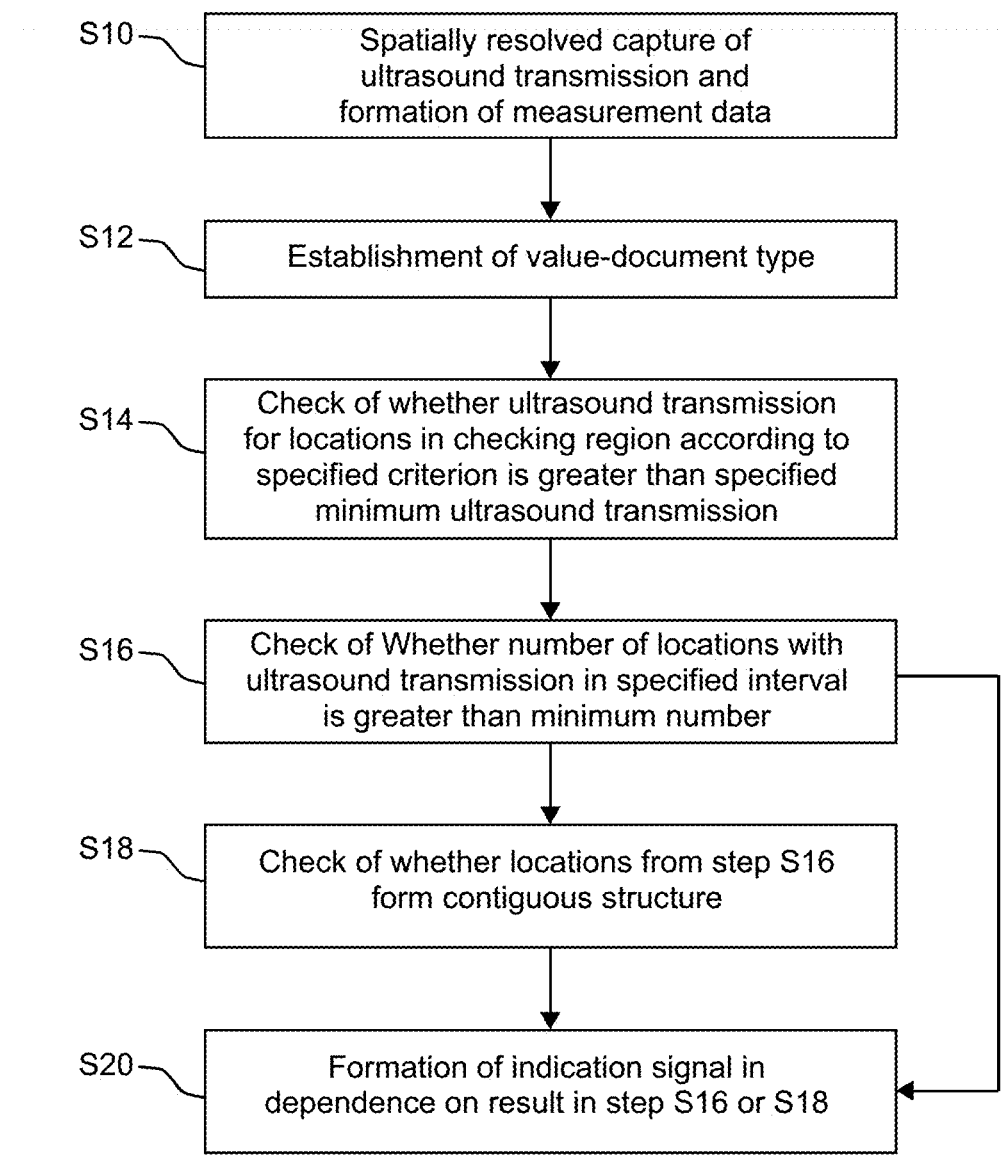

Starting out from these transmission values present for a value document as a function of location, the control and evaluation device 46, more precisely the processor 48, now carries out, when executing program code of the computer program stored in the memory 50, the following method for establishing the authenticity of the value document. The first step S10, however, is carried out partly by the ultrasonic sensor 44. The method is illustrated very schematically as a flowchart in FIG. 10.

Figure 6:
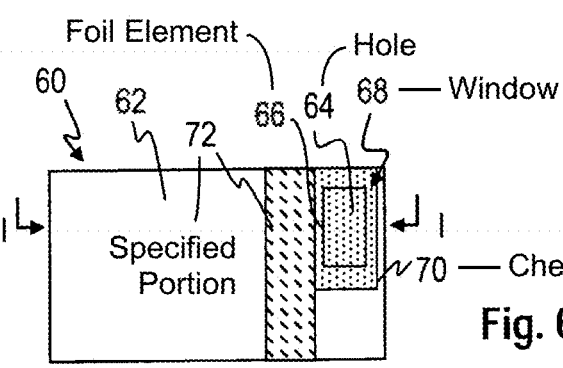
Figure 7:
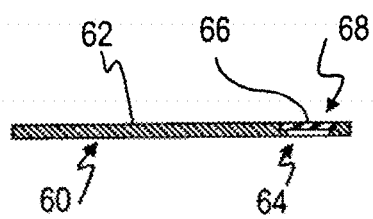

In the described exemplary embodiment, there is employed as the specified value-document type of value documents the type of bank note shown in FIGS. 6 and 7.

The bank note 60 comprises a substrate 62 made of bank-note paper which has at a specified place a rectangular hole 64 of specified size, in the example with a surface area of about 50 mm$^2$ Applied to the substrate 62 in the region of the hole 64 is a foil element 66 made of a polymeric material, whose weight per unit area is at least 10% lower than that of the substrate 62 in the surroundings of the hole 64 and which completely covers the hole 64. The covered hole 64 and the foil element 66 form a window 68.

In the method, there is employed, on the one hand, a checking region 70 which is so specified for the value-document type that the window 68 lies within the checking region 70 also within the framework of usual manufacturing fluctuations. Further, in the method, there is employed a minimum ultrasound transmission that is characteristic of a specified portion, lying outside the checking region, of at least one value document of the specified value-document type, and which in the present example is obtained by arithmetic averaging of the ultrasound transmission for locations in a specified region 72 of a few reference value documents of the specified value-document type. This region 72 lies outside the checking region 70 in which the window 68 lies and is preferably so chosen that it has a substantially location-independent ultrasound transmission, which preferably corresponds to the ultrasound transmission in the neighborhood of the window 68.

Further, in the method, there is employed an interval within which the ultrasound transmission or the ultrasound transmission value for locations in the window 68 must lie. The lower limit is chosen in dependence on the criterion for an ultrasound transmission being greater than the minimum ultrasound transmission. In the example, the lower limit is about 5% greater than the minimum ultrasound transmission. The upper limit is smaller than an ultrasound transmission that would be captured in the presence of a value document. In the present example, it is so chosen that it corresponds to the arithmetic average from the ultrasound transmission in the absence of a value document and an average over the reference value documents for the ultrasound transmission for a location in the window 68. These values are stored in association with the value-document type.

In step S10, measurement values for the ultrasound transmission of ultrasound of the ultrasonic sensor through the value document are established in a spatially resolved manner by means of the ultrasonic sensor and the control and evaluation device.

In step S12, the control and evaluation device 30 establishes whether the value document has a specified value-document type. If this is the case, the value-document type is stored for further employment. Otherwise, an error message is issued, whereupon the method is aborted. For establishing the value-document type there can be employed for example the data of one of the optical sensors. Methods for this purpose are known to the person skilled in the art. Further, the position of the value document is established.

In steps S14 and S16, the control and evaluation device 30 checks while employing the measurement values or transmission values whether for a specified number of locations in the checking region 70 specified for the value document the ultrasound transmission according to the specified criterion is greater than a specified minimum ultrasound transmission that is characteristic of the specified portion 72, lying outside the checking region 70, of a value document of the specified value-document type.

In step S14, the transmission values for locations in the checking region 70 are thus tested for whether the transmission values according to the specified criterion are greater than the specified minimum ultrasound transmission or a corresponding value. For this purpose, in the present example, the checking region is first specified in dependence on the value-document type and the recognized position. This is effected in the present example, on the one hand, by respectively forming for the locations to be checked an arithmetic average of the ultrasound transmission over the respective location and that over, in the example, six directly neighboring locations and employing it as the ultrasound transmission for the respective location. On the other hand, it is checked whether the thus formed averages or ultrasound transmissions lie within the interval specified for value documents of the specified type. The result of the check is stored for each location.

In step S16, it is checked whether the number of the transmission values for locations in the checking region 70 that lie within the interval is greater than the specified number. The number of the transmission values is specified in dependence on the type of the value document, in particular the surface area of the window and the spatial resolution of the ultrasonic sensor, and is to be regarded as a minimum number. For the check, the number of the transmission values established in step S14 and lying within the interval is established and compared with the minimum number. The result of the comparison is stored.

In this exemplary embodiment, it is additionally checked in step S18 whether the locations corresponding to the specified number of transmission values form a contiguous structure. For this purpose, the locations corresponding to the transmission values lying within the interval are established. Thereafter it is checked whether these locations include a group with at least the minimum number which form a contiguous region, i.e. whether each one of the locations of the respective group has at least one further one of the locations of the group directly neighboring thereto.

If the checks yield in the steps S16 that the specified number was reached and S18 that the locations associated with transmission values within the interval form a contiguous region, the control and evaluation device 30 forms in step S20 a signal which represents an indication of the authenticity of the security feature or of the value document.

Otherwise, the control and evaluation device 30 forms a signal which represents an indication of the presence of a forgery of the value document.

The signal leads to the storage of a corresponding authenticity indication value, e.g. in the memory of the control and evaluation device.

The signal or authenticity indication value is, as described hereinabove, used with corresponding signals or authenticity indication values for the other sensors for establishing the authenticity of the value document.

Figure 11:
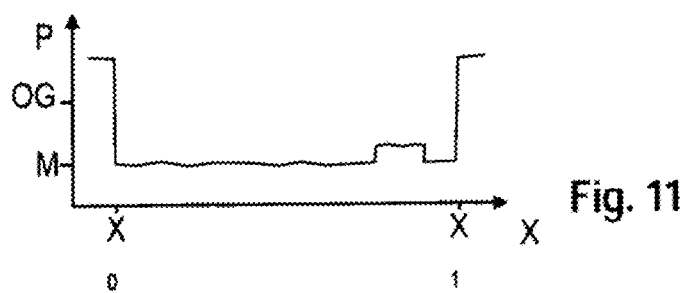

FIG. 11 shows for illustration schematically, in arbitrary units, the level P for the ultrasound transmission as a function of a coordinate X on the value document for a track along the line I-I in FIG. 6. FIGS. 6, 7 and 11 are so disposed and scaled that locations lying one below the other in the figures respectively correspond to each other along the line I-I. The value document begins at the coordinate $X_0$ and extends to the coordinate $X_1$. To the left of $X_1$ and to the right of $X_1$ a level is reached that is obtained upon reception of an unattenuated ultrasonic signal, i.e. in the absence of the value document. In the region of the window 68 the level is increased compared with the level for the remainder of the value document. Further, the minimum ultrasound transmission M is shown, and the upper limit of the interval OG. The lower limit is not drawn in, since it differs too little from M.

A second exemplary embodiment differs from the described first exemplary embodiment in that, in a step S13 between the unchanged step S10 and a step S14' replacing the step S14, the specified minimum ultrasound transmission is established on the basis of the captured transmission values for the value document, and therefrom the lower limit of the interval. The step S13 can be carried out before or after step S12. For this purpose, the control and evaluation device 30 establishes an arithmetic average over the transmission values or measurement values captured for locations in the portion 72, outside the checking region 70. This average, increased by 5% in the example, is set as the lower limit of the interval.

Other exemplary embodiments differ from the above-mentioned exemplary embodiments solely in that the step S18 is replaced by a step S18', and step S20 is adjusted accordingly. Such an exemplary embodiment modified relative to the first exemplary embodiment is shown schematically in FIG. 12. Unless otherwise mentioned, the steps with the same designation as in the first exemplary embodiment are also unchanged relative thereto.

In the step S18', it is not checked whether the locations corresponding to the specified number of transmission values form a contiguous structure, but rather the check also involves taking into consideration the distribution of those locations in the specified checking region for which the ultrasound transmission is greater than the minimum ultrasound transmission. Preferably, it is checked for this purpose whether the distribution of those locations in the specified checking region for which the ultrasound transmission is greater than the minimum ultrasound transmission satisfies a specified distribution criterion. In the present example, there is established for this purpose the smallest rectangle in which the stated locations lie, and the size of the rectangle is compared with the specified size of the window in value documents of the specified type. If the deviation of the length and width of the rectangle from the specified length or width of the window is smaller than a specified tolerance value, it is decided that the distribution satisfies the distribution criterion, otherwise it does not.

Step S20 is adjusted to the effect that if the checks in step S16, that the specified number was reached, and S18', whether the distribution of those locations in the specified checking region for which the ultrasound transmission is greater than the minimum ultrasound transmission satisfies a specified distribution criterion, turn out positive, the control and evaluation device 30 forms in step S20 a signal which represents an indication of the authenticity of the security feature or of the value document.

In other exemplary embodiments, both steps S18 and S18' can also be performed, an indication of authenticity resulting when both the check in step S18 of whether the locations form a contiguous structure and the check of the distribution of the locations in step S18' deliver a positive result.

Figure 12:
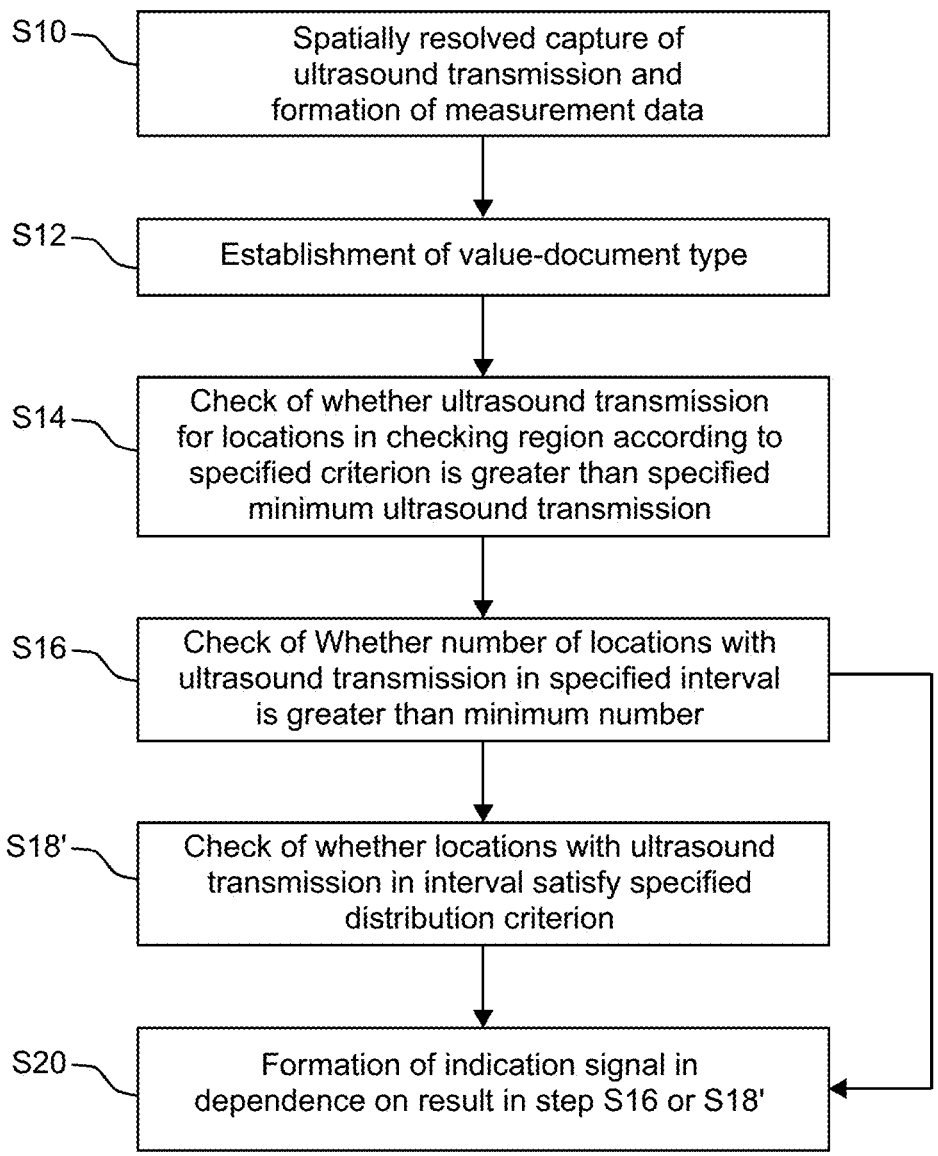
Figure 13:
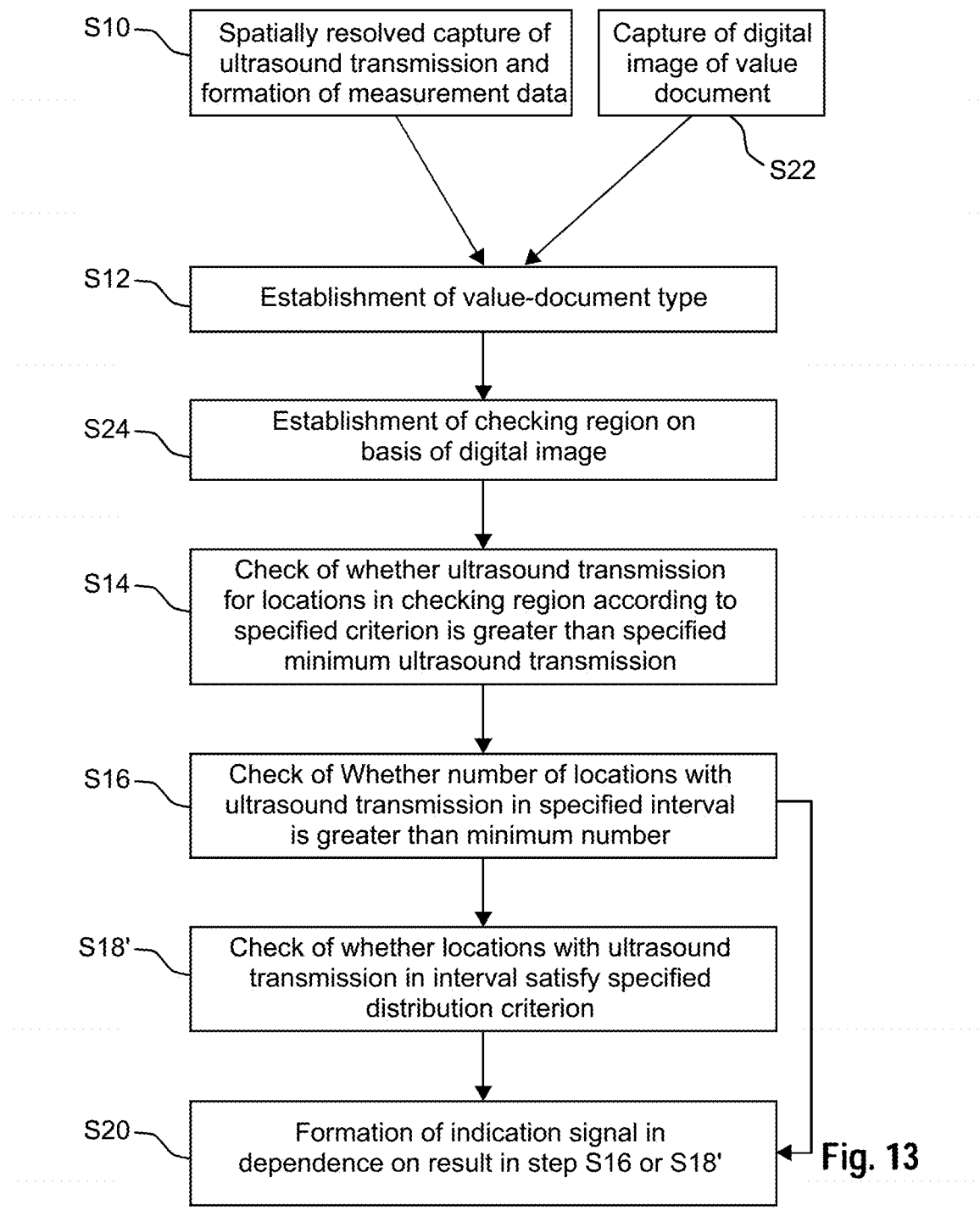

A further exemplary embodiment in FIG. 13 differs from the exemplary embodiment in FIG. 12 in that the checking region is fixed in dependence on a digital image of the value document. Unless otherwise mentioned in the following description of this exemplary embodiment, the steps with the same reference signs as in FIG. 12 are unchanged.

Before, during or after step S10, a digital image of the value document is captured by means of the optical transmission sensor 42 and the pixel data representing the digital image are stored in the control and evaluation device 46 in step S22. Preferably, this step S22 is performed before the step S12.

In step S12, the position of the value document does not necessarily need to be established.

Figure 14:
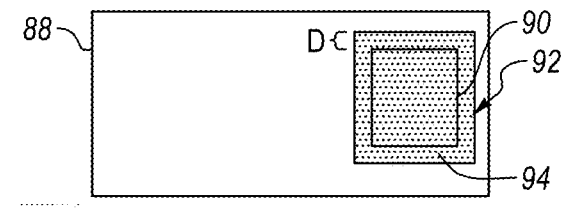

In dependence on the value-document type recognized in step S12, the checking region to be employed in the following steps is fixed in step S24. This is illustrated in FIG. 14 for a value document 88. In the digital image the position and size of the window 90 relative to the value document are established, employing for this purpose data known for the value-document type with regard to the window in the image of the value document. The checking region 92 is now so fixed in position and size that it comprises the window recognized in the digital image, and a frame region or edge region 94 enclosing the window and having a width D of 2 mm, in the example, said width being specified in dependence on the manufacturing tolerances and the ultrasonic frequency. Corresponding data are stored thereon in the control and evaluation device.

Figure 16:
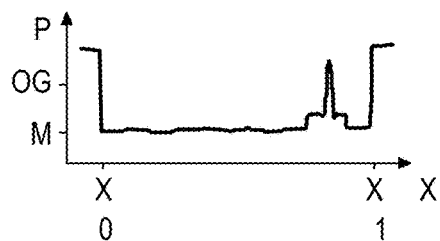

A further exemplary embodiment differs from the first exemplary embodiment in that there is additionally effected a check for the state of the window and in particular for whether the window 68 is damaged. Damage to the window, more precisely to the foil, leads to a substantially elevated transmission, as is illustrated very schematically in FIG. 16. Within the window region, which was described hereinabove, there is found in the example a peak which stems from a location in which the foil is interrupted, i.e. has a hole or tear. The value-document processing apparatus and in particular the control and evaluation device is then configured for processing, in this exemplary embodiment sorting, the value documents also in dependence on the state of the window.

Figure 15:
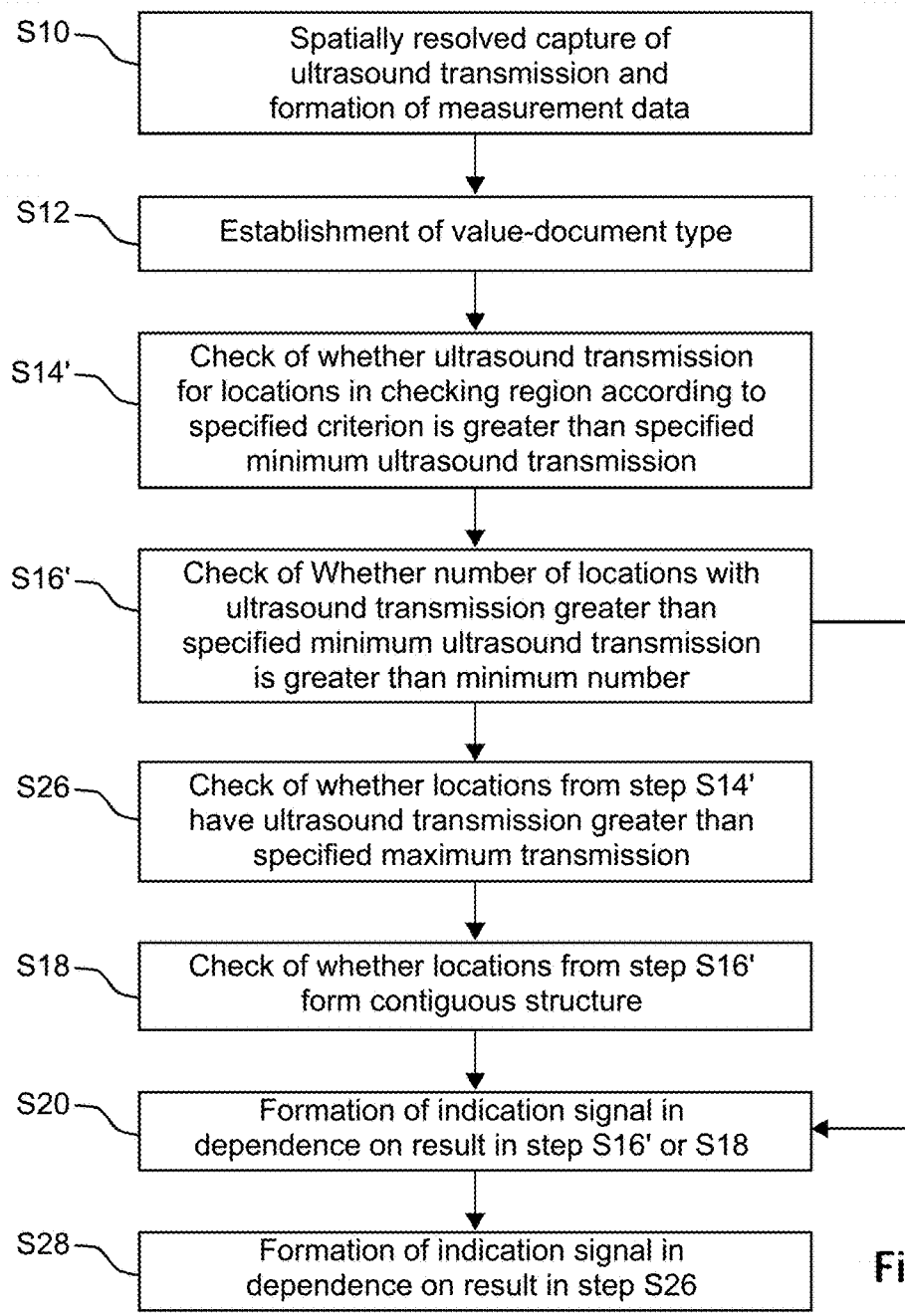

FIG. 15 shows very schematically the course of the method. The method differs from the method of the first exemplary embodiment by the steps S14", S16", S26, S18" and S28. The other steps are unchanged, except that instead of the results of one of the steps S14, S16 or S18 there are employed the corresponding results of the steps S14", S16" or S18". The further description of the stated steps in the first exemplary embodiment applies accordingly here too.

In step S14", it is checked, similarly to step S14 of the first exemplary embodiment, whether the ultrasound transmission for locations in the checking region according to the specified criterion is greater than the specified minimum ultrasound transmission. The step is changed compared with the step S14 in that, instead of checking whether the ultrasound transmissions lie within the interval, it is only checked whether they are greater than the minimum ultrasound transmission which serves for fixing the lower limit of the interval of the first exemplary embodiment. The result of the check is stored for each location, as in the first exemplary embodiment.

The step S16" differs accordingly from the step S16 only in that it is not checked whether the number of the ultrasound transmission values for locations in the checking region 70 that lie within the interval is greater than the specified minimum number; instead it is checked whether the number of the locations with an ultrasound transmission greater than the specified minimum ultrasound transmission is greater than the minimum number from step S16.

In the new step S26 it is now checked whether locations from step S14" have an ultrasound transmission that is greater than a specified maximum transmission. If such locations are found, this is an indication of damage to the window 68. The maximum transmission is specified in dependence on the value-document type and is greater than an ultrasound transmission that is characteristic of locations in a window of an undamaged value document of the specified value-document type. In the present example, it is so chosen that it corresponds to the arithmetic average from the ultrasound transmission in the absence of a value document and an average over the reference value documents for the ultrasound transmission for a location in the window 68. These values are already stored in association with the value-document type before the method is performed.

In the step S28, which does not necessarily need to be carried out after the unchanged step S20, the control and evaluation device forms in dependence on the result of the check in step S26 an indication signal or state signal which describes whether or not an indication of a damaged state of the window and thus of the value document or a damage to the window is present. If there is found in step S26 a specified number of locations, in this exemplary embodiment only one location, there is formed an indication signal which represents an indication of damage; otherwise an indication signal is formed which describes that an indication of an undamaged state of the window or no indication of damage was found.

The value document can be sorted in dependence on the two indication signals.

A further exemplary embodiment differs from the preceding exemplary embodiment by a further step in which it is checked whether locations found in step S26 form a contiguous structure. If this is the case, there is additionally formed in step S28 a signal which indicates the number of the locations, optionally also the form of the structure classified as "tear" or "hole".

Further exemplary embodiments differ from the above-described exemplary embodiments in which it is checked whether the ultrasound transmissions lie within the specified interval, in that all checks in which it is checked whether the ultrasound transmission lies within the specified interval are replaced by the check corresponding to step S14". The results of these changed steps are employed in the following steps. The steps S26 and S28 can then be taken over from the exemplary embodiment in FIG. 15.

Yet further exemplary embodiments differ from the above-described exemplary embodiments in that in step S12 the position of the value document is not established, but instead the steps S14 and S16 or S14" and S16" are carried out for the four possible positions. Only if at least one of the checks yields an indication of a window, a corresponding indication signal is then formed.

Figure 8:
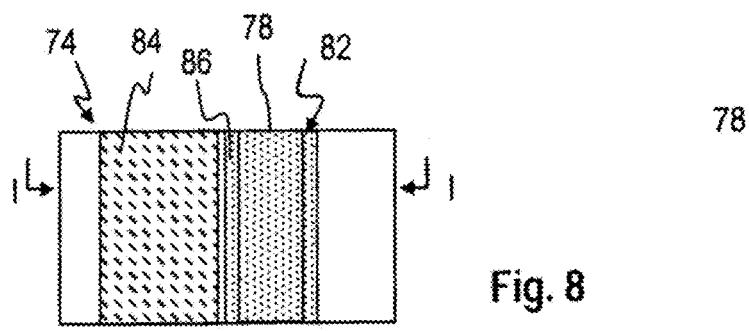
Figure 9:
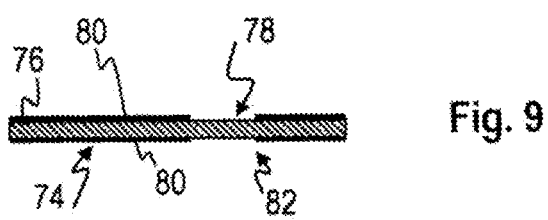

In other exemplary embodiments there can be employed as value documents value documents of a value-document type that have a substrate made of a polymer foil, for example biaxially stretched polypropylene, having a see-through window. A value document of this value-document type is shown by way of example and schematically in FIGS. 8 and 9. The value document 74, a bank note, comprises the substrate 76 which is formed by the polymer foil. On both sides of the substrate 76 there are located, over the entire area except for a region 78, opacifying cover layers 80 applied by printing technology which carry the printed image of the bank note. The region 78 is transparent, however, since it is not covered by the cover layers 80. The region 78 hence forms a see-through window 82 of the bank note. The above-mentioned exemplary embodiments can be adjusted for this value-document type. The region serving for establishing the minimum ultrasound transmission can be for example the region 84 shown in FIG. 8, and the checking region the dotted region 86.

The invention claimed is:

1. A method for checking a value document of a specified value-document type having a window which has a foil region, the method comprising:
capturing ultrasound transmission properties using a spatially resolving ultrasound transmission sensor that establishes measurement values for an ultrasound transmission of the value document in a spatially resolved manner;
defining a specified outside portion which lies outside of a checking region of the value document, the outside portion comprising some, but not all of, the value document;
checking, while employing the measurement values, whether for a specified number of locations in the specified checking region of the value document the ultrasound transmission according to a specified criterion is greater than a specified minimum ultrasound transmission that is characteristic of the specified outside portion of the value document; and
as a result of the checking, generating a signal describing the result of the checking.

2. The method according to claim 1, wherein the ultrasound transmission has a frequency in the range of 50 kHz to 800 kHz.

3. The method according to claim 1, wherein the specified minimum ultrasound transmission was established by examinations of reference value documents of the specified value-document type.

4. The method according to claim 1, wherein before the check the specified minimum ultrasound transmission is established while employing measurement values captured for the value document.

5. The method according to claim 1, wherein it is checked whether for locations in the checking region the ultrasound transmission is greater than a specified maximum transmission which is greater than an ultrasound transmission that is characteristic of locations in a window of an undamaged value document of the specified value-document type.

6. The method according to claim 5, wherein, if the checking yields that the ultrasound transmission for at least one of the locations exceeds the maximum transmission, the signal indicates that the window is damaged.

7. An apparatus for processing value documents comprising a feeding device for feeding singled value documents, an output device for receiving processed value documents, a transport device for transporting singled value documents, fed by the feeding device, along a transport path from the feeding device to the output device, and an examination apparatus having an ultrasound transmission sensor for capturing spatially resolved measurement values for the ultrasound transmission through the value document, and a control and evaluation device connected to the ultrasound transmission sensor via a signal connection, which is configured for carrying out a method according to claim 6.

8. The method according to claim 5, further comprising additionally checking whether a plurality of locations for which the ultrasound transmission is greater than the maximum transmission form a contiguous structure.

9. An apparatus for processing value documents comprising a feeding device for feeding singled value documents, an output device for receiving processed value documents, a transport device for transporting singled value documents, fed by the feeding device, along a transport path from the feeding device to the output device, and an examination apparatus having an ultrasound transmission sensor for capturing spatially resolved measurement values for the ultrasound transmission through the value document, and a control and evaluation device connected to the ultrasound transmission sensor via a signal connection, which is configured for carrying out a method according to claim 8.

10. The method according to claim 1, wherein the check involves establishing whether the respective ultrasound transmission lies within a specified interval whose lower limit is greater than the specified minimum ultrasound transmission.

11. The method according to claim 1, wherein the check also involves taking into consideration the distribution of those locations in the specified checking region for which the ultrasound transmission is greater than the minimum ultrasound transmission.

12. The method according to claim 1, wherein it is additionally checked whether the locations for which the ultrasound transmission is greater than the minimum ultrasound transmission and/or for which the ultrasound transmission lies within the specified interval form a contiguous structure, and/or wherein it is additionally checked whether a plurality of locations for which the ultrasound transmission is greater than the maximum transmission form a contiguous structure.

13. The method according to claim 1, wherein a digital image of the value document is captured by means of an optical sensor, and the checking region is specified while employing the image.

14. The method according to claim 1, wherein the window comprises a hole in a paper substrate or hybrid substrate of the value document and at least one foil covering the hole.

15. The method according to claim 1, wherein the window is given by a region of a value document having a polymer substrate, said region having no opacifying layer.

16. An apparatus for examining a value document of a specified value-document type having a window, said apparatus having an ultrasound transmission sensor for capturing spatially resolved measurement values for the ultrasound transmission in a specified frequency range through the value document, and a control and evaluation device connected to the ultrasound transmission sensor via a signal connection, which is configured for carrying out a method according to claim 1.

17. An apparatus for processing value documents having a feeding device for feeding singled value documents, an output device for receiving processed value documents, a transport device for transporting singled value documents, fed by the feeding device, along a transport path from the feeding device to the output device, and an examination apparatus according to claim 16, wherein the transport path extends through the ultrasound transmission sensor, with the apparatus for processing value documents being configured for processing including sorting, the value documents in dependence on signals of the examination apparatus.

18. The method according to claim 1, wherein the signal represents an indication of the authenticity of the value document and/or which represents an indication of the presence of a forgery of the value document.

19. An apparatus for processing value documents comprising a feeding device for feeding singled value documents, an output device for receiving processed value documents, a transport device for transporting singled value documents, fed by the feeding device, along a transport path from the feeding device to the output device, and an examination apparatus having an ultrasound transmission sensor for capturing spatially resolved measurement values for the ultrasound transmission through the value document, and a control and evaluation device connected to the ultrasound transmission sensor via a signal connection, which is configured for carrying out a method according to claim 18.

\* \* \* \* \*